United States Patent [19]

Kesling

[11] 4,330,273
[45] May 18, 1982

[54] ORTHODONTIC APPLIANCE AND METHOD FOR PRODUCING OCCLUSION

[76] Inventor: Peter C. Kesling, Green Acres, LaPorte, Ind. 46350

[21] Appl. No.: 170,683

[22] Filed: Jul. 21, 1980

[51] Int. Cl.³ .............................................. A61C 7/00
[52] U.S. Cl. ....................................................... 433/5
[58] Field of Search ........................................ 433/5, 6

[56] References Cited

U.S. PATENT DOCUMENTS

| | | | |
|---|---|---|---|
| 2,086,656 | 7/1937 | Woodward | 433/18 |
| 3,837,081 | 9/1974 | Kesling | 433/6 |
| 4,139,944 | 2/1979 | Bergersen | 433/6 |

Primary Examiner—Robert Peshock
Attorney, Agent, or Firm—Lloyd L. Zickert

[57] ABSTRACT

An orthodontic appliance comprising a resilient member arranged to be positioned between the upper and lower arches and force-generating elements applying forces to at least some of the teeth of at least one of the arches. The resilient member is made over an orthodontic setup or a model having ideal arch form and includes sockets for the occlusal surfaces of the teeth of each of the arches arranged such that when the teeth seat in the sockets, they will be in the ideal or best possible occluding positions relative to each other. Any suitable type of force-generating means may be used to apply traction to one or more of the teeth of one of the arches toward the teeth of the other of the arches.

10 Claims, 12 Drawing Figures

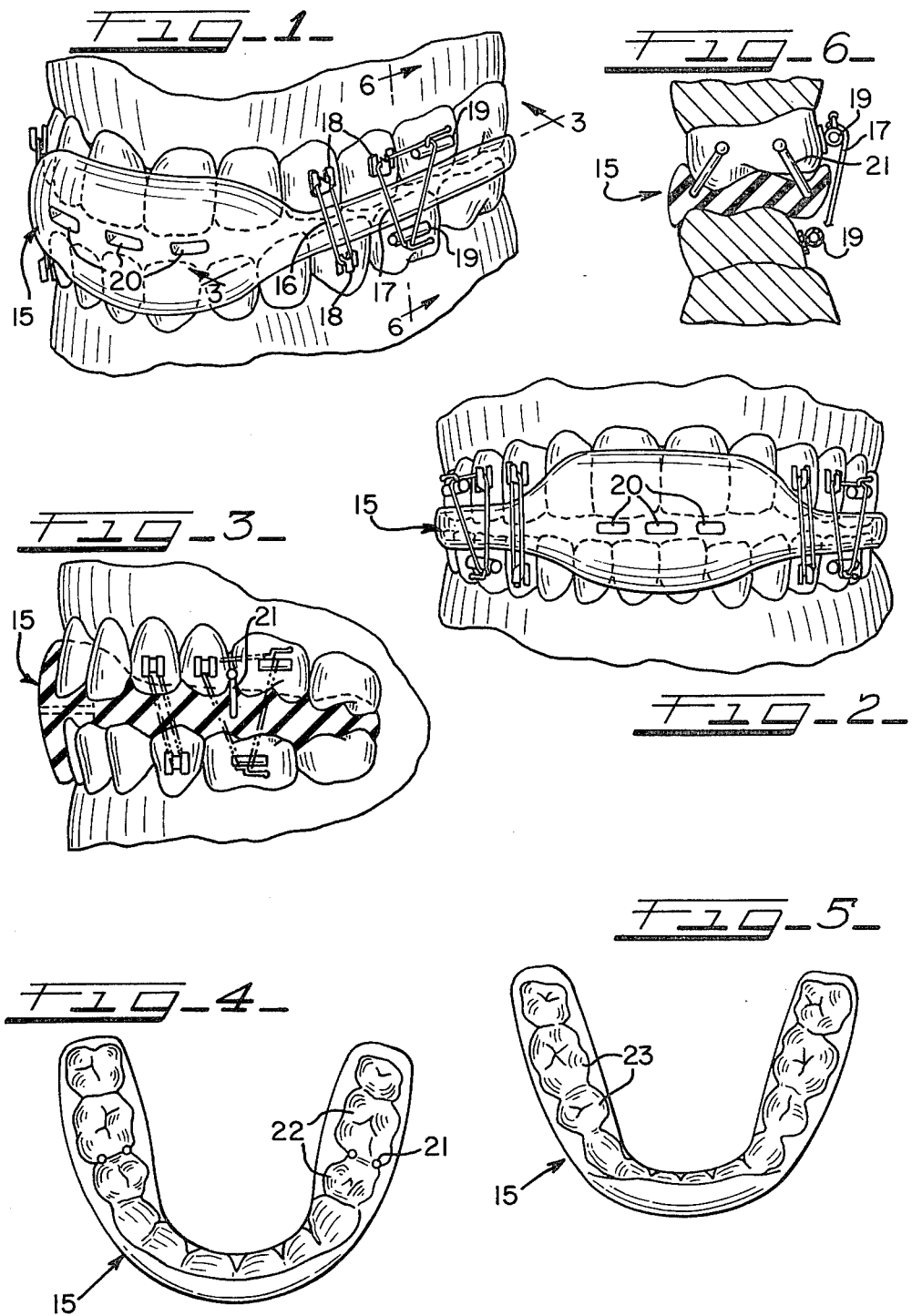

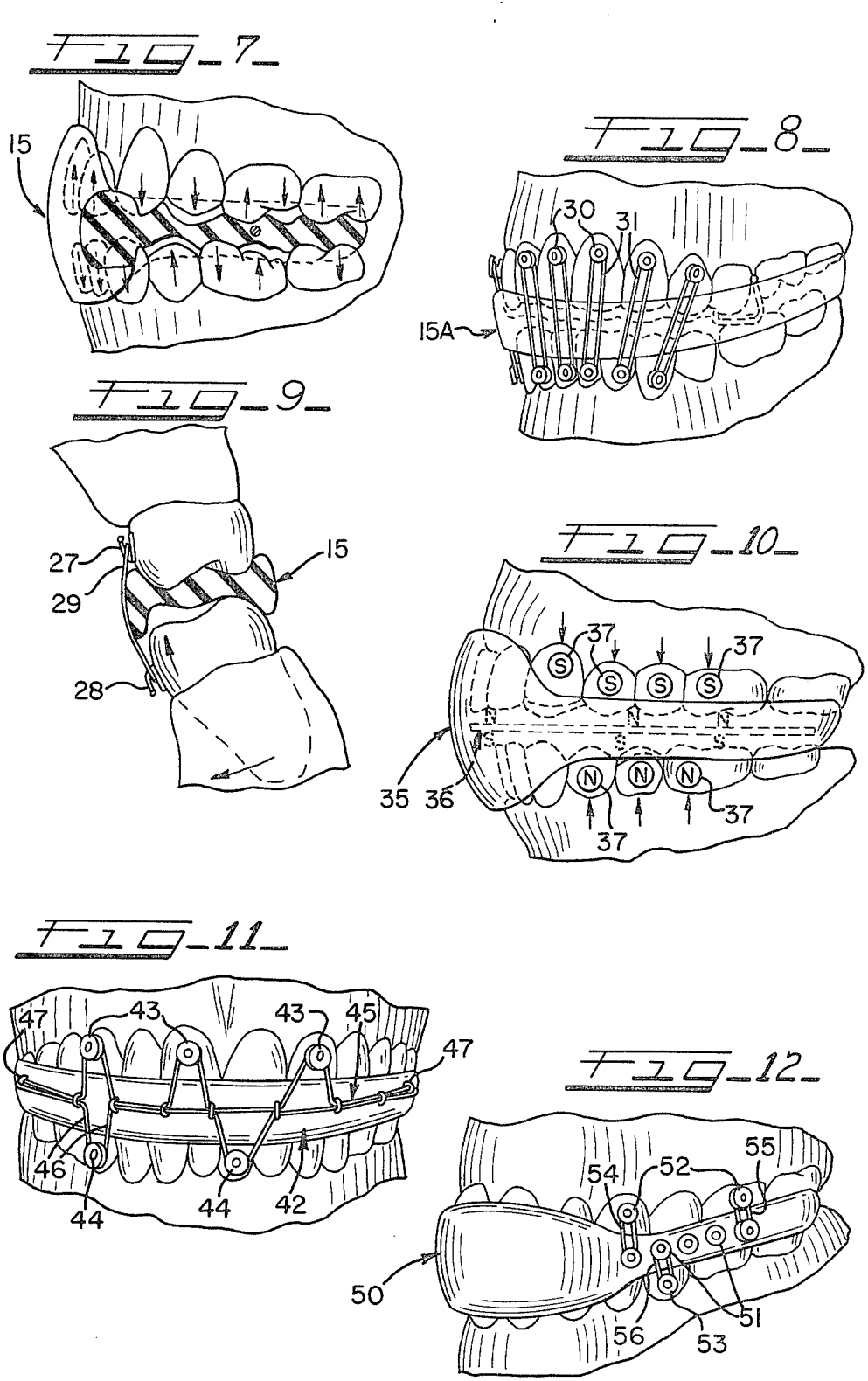

ORTHODONTIC APPLIANCE AND METHOD FOR PRODUCING OCCLUSION

This invention relates in general to an orthodontic appliance, and more particularly to an orthodontic appliance for producing the best possible or ideal occlusion between teeth of the arches, and still more particularly to an orthodontic appliance including a resilient member arranged to fit between the teeth and force-generating means for applying traction forces to the teeth to cause them to properly seat on the resilient member.

There has been a growing interest in orthodontics to develop a method or system for accomplishing "precision" orthodontic treatment to achieve the best possible and preferably ideal results for a given patient. One of the systems presently being marketed and generally referred to as the "straight wire" system involves the use of brackets having archwire receiving slots at varying degrees of three-dimensional inclination, it being intended that with the accurate placement of a bracket on each tooth a straight archwire, or one having no bends for individual teeth, may be placed in the bracket slots for each arch, thereby applying forces to the teeth with the intention that they will automatically be brought to their ideal positions relative one another. This system, however, works on the premise that the angles of the archwire slots or tubes are manufactured for the average or normal shape and size of a particular tooth.

The disadvantage of the straight wire system is that no given patient has all teeth equal to or even near equal to the average shape or size from which the manufacturer predetermines the various angulations or positions of archwire receiving slots and tubes.

Moreover, it is either impossible or clinically impractical to accurately mount the attachments onto the patient's teeth to take advantage of the dimensional and angular differences between archwire slots having incremental differences on the order of five degrees and dimensional differences on the order of 0.001 inch. In any event, if an attachment becomes bent or requires replacement during the course of treatment, the "precise" nature of the original placement has been lost or nearly impossible to duplicate within the tolerances required of the system. Research and study of the various shapes and sizes of teeth used to determine proper placement of each orthodontic attachment cannot possibly account for the unique individuality of each patient's occlusal surfaces as these are as distinct as fingerprints. Accordingly, it may be appreciated that the ultimate goal of orthodontic treatment—the best occlusion possible between the upper and lower teeth—is not anticipated, planned for, or even possible when only the labial/buccal surfaces of teeth are used to determine proper attachment, design and location of same on each tooth.

Moreover, patients often have fillings placed in their teeth during the course of orthodontic treatment which can change the shapes and sizes of the teeth and especially their occlusal anatomy. It is not possible to allow for or account for this possibility in the "straight-wire" precision orthodontic techniques employed.

Additionally, employment of straight-wire techniques requires the orthodontist to carry expensive large inventories of brackets and tubes in order to orthodontically treat with the system. For example, up to twenty different kinds of brackets including those for upper and lower teeth and right and left sides are needed.

There is only one way to predict or predetermine the best possible occlusion for each patient prior to that occlusion being achieved in the mouth of a patient, and that is to construct an othodontic setup. The setup is constructed by taking impressions of the teeth of the patient, making models of the teeth from the impressions, removing one or more of the teeth from the models, and replacing the tooth or teeth in the best or most ideal position or positions for achieving the best or most ideal occlusion possible. The making of an orthodontic setup has been well known.

Should all the permanent teeth to be included in orthodontic treatment have erupted prior to commencement of orthodontic treatment, the setup can be made at that time. However, impressions can be taken at any time after the commencement of orthodontic treatment so that models can be made from the impressions and a setup can be made from the models. Normally, impressions and a setup are made at a time close to the termination of orthodontic treatment when less moement of the patient's teeth will be required to produce the ideal occlusion in the setup.

Another known approach to the precise treatment technique requires the construction of an orthodontic setup prior to commencement of orthodontic treatment. The brackets and tubes to be used are then oriented on the teeth of the setup by use of a "straight" wire or at least so that a "straight" wire can be received by all attachments on each arch without being deflected. Jigs or fixtures or the like are then employed to transfer the attachments from their positions on the teeth of the setup to the same locations on the respective teeth in the patient's mouth. If the transfer of the attachments is accurately accomplished and none of the attachments become bent or displaced during the course of treatment, and the occlusal anatomy does not change through fillings or wear, then it should be possible to achieve an occlusion in the patient's mouth that is the same as that on the original setup. However, experience has proven that these desired goals cannot be achieved, as it is extremely difficult if at all possible to accurately transfer the attachments from their positions on the teeth of the setup to the teeth in the patient's mouth, and during treatment at least one or more of the attachments may become bent or displaced and frequently the occlusal anatomy is changed by fillings. Thus, the desired accuracy and degree of precision sought by this approach cannot be clinically achieved. The variables present interfere with the very precision desired.

Still another approach to the seeking of precision treatment is to use a custom-made tooth-positioning appliance of the type disclosed in U.S. Pat. No. 3,178,820 made from an orthodontic setup and placed in a patient's mouth with instructions on how to use it. While the sockets of the teeth in the tooth-positioning appliance are in the ideal locations, arch-wise and occlusal-wise, use of the appliance requires active patient application of biting forces into the appliance. If patient cooperation is at its best, a leveling of the teeth can be accomplished through the application of depressive forces on the high portions of teeth by the patient biting into the appliance. Since eruptive forces cannot be generated by the biting into the appliance, the best possible occlusion is often difficult or impossible to attain. It should also be appreciated that a tooth-positioning appliance is constructed so that the sockets in the appliance cover all of the occlusal as well as substantially all of the labial/buccal and lingual surfaces of the teeth.

It has also been known to construct custom tooth-positioning appliances with metal adjuncts of various types to assist in the proper seating of the appliance in the mouth of a patient so as to obtain better ultimate results. Examples of such tooth-positioning appliances include the one disclosed in the aforementioned U.S. Pat. Nos. 3,178,820 and U.S. Pat. 3,407,500. It has further been known to make a custom tooth-positioning appliance adapted to be worn by a patient who still retains buccal tubes on the anchor teeth wherein the appliance would have sockets for receiving the buccal tubes, the primary purpose being to assist in seating the appliance on the teeth when worn by the patient. While tooth-positioning appliances of this type as previously indicated would also be capable of effecting depressive forces on teeth when a patient actually exercises into the positioner, they are not designed to apply eruptive forces on the teeth to obtain the best possible occlusion. Accordingly, the ultimate in precision treatment is not easily obtained from these appliances.

The present invention has the same purpose or goal as those previously mentioned, that is, to obtain precision finishing. However, it is much simpler to use and it eliminates the problems caused by possible changes in bracket position and/or occlusal anatomy during the course of treatment. Moreover, it not only induces patient cooperation by withholding their reward of total fixed appliance removal until successful results are achieved but eliminates the need for the patient to actively supply energy during use of the appliance by providing an energy source.

A method and an appliance are embraced by the present invention for producing the best possible occlusion. A custom-made individualized orthodontic setup is constructed from impressions made of the teeth preferably at a time near the end of regular fixed appliance orthodontic treatment. As already mentioned, an orthodontic setup is the only means by which to accurately predict and properly direct a patient's teeth to the ultimate goal of the best occlusion possible. The present invention was conceived in light of the known advantages of accurately predicting the best occlusion possible through a custom-made orthodontic setup and taking into account the problems and shortcomings of known approaches to precision finishing through both fixed and removable appliances. The present invention combines the advantages of fixed appliances with the advantages of removable appliances and eliminates the disadvantages of both, thereby achieving a consistent and unexpected "precision finishing" technique and result.

A removable resilient appliance is made over the orthodontic setup and in that respect is like the known tooth-positioning appliance. However, it differs in that it only includes occlusal receiving sockets for most of the teeth arranged in the ideal arch and occlusion positions and accommodates an energy source or means for applying directly eruptive and indirectly depressive forces to the teeth to move the teeth into fully seated position in the appliance. The energy source is applied by any number of means and methods such as by use of elastic means in the form of rubber bands or elastic thread that is suitably connected to fixed appliances on the teeth in the presence or absence of archwires held by the fixed appliances, and for applying pulling or traction forces on the teeth toward the appliance situated between the arches. In this respect it may be readily appreciated that the combination resilient appliance situated between the arches designed to improve the occlusal relationship of the arches through the movement of teeth and the energy source means of the system is passive to the patient and does not require active energy generation by the patient. By being able to produce pulling forces on the teeth toward the appliance situated between the arches, eruptive forces will be applied to those teeth that are "low", while depressive forces will be applied to those teeth that are "high".

While the hoped-for goal—ideal or best possible occlusion—from the unique application of the novel approach of the present invention to orthodontic finishing is not new, the results achieved through clinical testing are above and beyond any experienced orthodontist's expectations. The clinical testing shows that consistent positive improvement in patient occlusions are near the 100 percent level. The results are better than what could be expected from fixed appliances alone because the mechanical inhibitions and restrictions inherent in fixed appliances have been eliminated. Moreover, the clinical results are better than what could be expected from removable appliances such as tooth-positioning appliances because active use of the appliance by the patient to supply energy by biting into the appliance is not necessary, as the upper and lower arches and/or any of the individual teeth as required are continually drawn together by a renewable untiring source of energy that may not be a part of the removable appliance itself.

Use of the present invention for accomplishing the ideal or best possible occlusion requires the use of certain fixed attachments on the teeth. Patient acceptance is materially improved to accomplish the end result and induce the patient to use the present invention so that the fixed appliances can be removed. Additionally, manipulation on the part of the orthodontist is reduced and ultimately the rapidity and accuracy of tooth movements excel those previously known.

It is well known by orthodontists that brackets and tubes attached to the teeth are meant to accept archwires fashioned either to apply pressure to move the teeth and/or to act to guide the teeth as they move from other sources of force, such as elastics or springs. Usually, when the orthodontist determines that the time in the treatment has come to employ a removable and/or finishing and/or retaining appliance such as a tooth positioner, whether it be custom-made or preformed, or a retainer, all attachments are removed from the teeth prior to the placing of the removable appliance. Exceptions to removal of all attachments have included the retention of attachments for fitting into a resilient and removable appliance, such as suggested in U.S. Pat. No. 4,160,322 and as suggested by manufacturers of tooth-positioning appliances as well as use of molar locks shown in U.S. Pat. No. 3,407,500. These devices and systems are intended to enhance retention and possible activation of tooth-positioning appliances. It has also been known that orthodontists leave attachments on the teeth and without placing anything between the teeth apply rubber bands to solely vertically move teeth without concern for the ideal occlusal plane and to merely cause the teeth to contact one another at any vertical level.

However, it has not been known to allow the attachments used in the initial stages of orthodontic treatment to remain fixed to all or some of the teeth for the sole purpose that they receive vertically directed elastics to erupt the teeth to predetermined levels established in an orthodontic setup. Similarly, it has never been known that with some or all of the attachments remaining fixed to the teeth with an archwire engaged in those attachments on one or both arches, with or without root-moving forces being applied continuously to the root or roots of one or more teeth in one or both arches, that a one-piece resilient appliance could be worn intermittently in conjunction with vertical elastics to achieve arch occlusion.

Heretofore, archwires connected to attachments fixed to the teeth function either through the manual bending of the archwire or the original vertical placement of the attachments to produce vertical movement of the teeth to bring the occlusal surfaces to a point of better occlusion between the arches. The inter-occlusal resilient portion of the present invention acts as a custom archwire in that the teeth are induced to move toward their seated position in the occlusal sockets of the resilient portion. Thus, a leveling of the arch is accomplished by applying both occlusal, incisal and gingival forces to the teeth, and the resilient member acts as a stop or a goal which the teeth are pulled into ultimately by the continuous forces from the elastics or other suitable eruptive power source. It is therefore not necessary that the patient exercise into the appliance during the wearing of same.

In order to obtain an understanding of the present invention and its differences between it and the well known tooth-positioning appliance, it is necessary to understand both the similarities and the differences. The present invention includes a one-piece resilient appliance that is constructed over a setup and which may or may not have seating springs. With respect to this part of the present invention, the tooth-positioning appliance is the same. Further, the present invention is employed at the end of treatment as is a tooth-positioning appliance, and both have the same ultimate goal, that is, to obtain the best possible occlusion. However, the tooth-positioning appliance requires the use of the patient's masseter muscles as the major energy source, while the present invention utilizes elastics or the like as the major energy source. Further, the present invention applies pulling forces to most of the malpositioned teeth, while the tooth-positioning appliance applies pushing forces to the highest teeth. Since the tooth-positioning appliance is used without the attachments on the labial/buccal surfaces of the teeth, it is impossible to continually control root movements while adjusting the teeth vertically. The present invention can be used with an archwire in one or both arches so that continued control of root movement can be controlled while adjusting the teeth vertically. The tooth-positioning appliance may be easily displaced from one or both of the arches especially when seating springs are utilized, while the resilient portion of the present invention cannot be accidentally displaced or removed. Little or no vertical movement of teeth can be obtained with a tooth-positioning appliance without active patient cooperation, while vertical movement of teeth can be obtained with the present invention without active patient cooperation. A tooth-positioning appliance is usually employed in the absence of any fixed attachements to the teeth, while those fixed attachments must be used during the use of the present invention. Accordingly, if all of the fixed attachements are removed for use of a tooth-positioning appliance, it is necessary to replace those fixed appliances if it is desired to return to fixed attachment thereapy, while the present invention allows immediate return to fixed attachment therapy because most of the fixed attachements have not been removed. When utilizing a tooth-positioning appliance, the motivation to use it is low inasmuch as the fixed attachments have already been removed. However, with the present invention patients are motivated to wear the appliance because most of the fixed attachments have not yet been removed, and it is that reward which is held out for obtaining complete patient cooperation to use the present invention so that the fixed appliances can be removed. The tooth-positioning appliance is designed to cover substantially all of the labial/buccal surfaces of the teeth, while the present invention includes a resilient member which does not cover all of the labial/buccal surfaces of the teeth and which does not cover those surfaces having fixed attachments so that the attachments are fully exposed and available for use and for connecting elastics between the arches.

it is also well known through studies of attritional occlusion that it is more natural for a tooth to erupt than to be depressed as they normally erupt throughout life. Accordingly, lighter forces can be used for obtaining eruption than for obtaining depression, and it is the intent of the present invention to generally obtain eruption, and therefore the present invention more quickly and easily obtains the desired end results.

It is therefore an object of the present invention to provide a new and improved orthodontic appliance and method for producing the best possible occlusion when finishing up orthodontic treatment of a patient.

It is a further object of the present invention to provide an orthodontic appliance and method for producing the best possible occlusion at the end of orthodontic treatment which uses elastics or the like as a major energy source for accomplishing the desired occlusion results.

It is a still further object of the present invention to provide a new and improved orthodontic appliance and method for producing the best possible occlusion which applies eruptive forces directly to some of the teeth and depressive forces indirectly to other of the teeth.

Another object of the present invention provides an orthodontic appliance and method for producing the best possible occlusion which also allows continuing controlled root movement while adjusting the teeth vertically to the best possible occlusion.

A further object of the present invention is to provide an orthodontic appliance and method for producing the best possible occlusion which when worn by the patient cannot be accidentally displaced or removed and which therefore will achieve the ultimate occlusion results quicker and easier.

Another object of the present invention is to provide an orthodontic appliance and method for producing the best possible occlusion which when worn by the patient will not require active patient generation of energy for reaching the ultimate results.

A still further object of the present invention is to provide an orthodontic appliance and method for producing the best possible occlusion which facilitates the return to complete fixed appliance thereapy if desired.

Another object of the present invention is to provide an orthodontic appliance and method for producing the best possible occlusion which motivates patients to cooperate as fixed attachments remain on the teeth during use and it is a desire of the patient to have those attachments removed.

Other objects, features and advantages of the invention will be apparent from the following detailed disclosure, taken in conjunction with the accompanying sheets of drawings, wherein like reference numerals refer to like parts, in which:

FIG. 1 is a perspective view of the appliance of the present invention in mounting relation on the teeth of a patient;

FIG. 2 is a front elevational view of the appliance of the present invention as mounted on the teeth of a patient;

FIG. 3 is a side elevational view of the appliance while showing the appliance in section in a manner in which it coacts with the teeth of the arches and taken generally along line 3—3 of FIG. 1;

FIG. 4 is a top plan view of the interocclusal portion of the appliance of the invention;

FIG. 5 is a bottom plan view of the interocclusal portion of the appliance of the invention;

FIG. 6 is a vertical sectional view taken generally along line 6—6 of FIG. 1;

FIG. 7 is a view similar to FIG. 3 but illustrating schematically the manner in which forces are applied to the teeth in order to bring them into the occlusion designed by the resilient appliance positioned between the teeth;

FIG. 8 is a modified version of the present invention wherein forces are applied to the anterior teeth for obtaining elongation thereof;

FIG. 9 is a vertical sectional view taken through an appliance similar to FIG. 6 but illustrating how attachments may be utilized on the lingual surfaces of the teeth for receiving elastic means to obtain occlusion;

FIG. 10 is a further modified version of the present invention wherein magnets are employed for developing the energy source for movement of the teeth along the vertical;

FIG. 11 is a further modified version of the present invention wherein elastic means are extended from the interocclusal resilient appliance to attachments on the teeth for applying the eruptive forces; and FIG. 12 is a further modified version of the present invention wherein attachments are provided on the interocclusal resilient member as well as on the teeth for receiving elastics to again apply pullying forces to preselected teeth so that they move toward seated positions in the interocclusal appliance.

Referring now to the drawings and particularly to the embodiment in FIGS. 1 to 7, the present invention includes a resilient appliance 15 adapted to be worn interocclusally between the upper and lower arches of the user, and means for directly generating eruptive forces on preselected teeth which includes, as illustrated in this embodiment, rubber bands or elastics 16 and 17 and anchoring means in the form of brackets 18 and tubes 19. The generation of eruptive forces will indirectly generate depressive forces on those teeth fully or partly engaging the occlusal receiving surfaces of the appliance.

The resilient appliance or member 15 is constructed over an orthodontic setup in a well known manner such as disclosed in U.S. Pat. No. 2,467,432, wherein following the taking of impressions of teeth of a patient, models of the teeth are made, one or more of the teeth on the models are removed and reset such that the teeth are in the ideal arch and occlusal positions to provide the best possible occlusion, thereby defining the orthodontic setup, and the resilient appliance is molded to fit the setup. The resilient appliance 15 may be molded from any suitable material such as a natural or synthetic rubber or a plastic which will provide the desired resiliency. In this respect the appliance 15 is custom-made over an orthodontic setup. However, it should be appreciated that a mass-produced non-custom version of this appliance could be used. Additionally, the air holes 20 may be formed in the appliance in a manner as illustrated in U.S. Pat. No. 4,194,046.

The appliance 15 may optionally have seating springs such as indicated by the numeral 21 in FIGS. 3 and 6 which would assist in the proper placement and retention of the appliance in the mouth when it is placed there by the user to assure proper orientation and seating to the teeth. Appliances with seating springs are illustrated in U.S. Pat. Nos. 3,178,820 and 3,837,081. Each seating spring includes a pair of arms projecting into the archways of the appliance for engagement in embrasure areas of the teeth.

The resilient appliance 15 is arch-shaped and would have upper and lower archways with tooth sockets 22 formed in the upper archway and tooth sockets 23 formed in the lower archway with resilient material situated between and separating the archways, as illustrated particularly in FIGS. 3, 6 and 7. It will be understood that the use of "tooth sockets" herein is intended to primarily define a structure for receiving the occlusal surfaces of the teeth. The embodiment of FIGS. 1 and 2 includes only occlusal receiving surfaces along the buccal, while the sockets along the labial additionally have partial labial receiving surfaces. Further, it should be appreciated that the archways may be formed like those in the positioner illustrated in U.S. Pat. No. 3,724,075. However, the resilient appliance 15 would differ from this appliance and other in that it would be made for accommodating the energy producing means, rubber bands in this embodiment, that would need to be connected between attachments on the upper and lower arches, as illustrated in FIGS. 1 and 2. It is necessary that each of the sockets 22 and 23 has mating surfaces for all of the occlusal surfaces of the teeth and at least part of the labial/buccal and/or lingual surfaces of some of the teeth. It is further necessary that where the rubber bands are to be used the appliance 15 exposes substantially all of the labial/buccal or lingual surfaces of those teeth which would have attachments to which the rubber bands are to be attached so that there is no interference between the appliance and the attachments on the teeth. This will be noted particularly in FIG. 1 wherein the buccal side of the appliance 15 does not touch or interfere with any of the attachments 18 and 19, and thereby facilitates the interconnection of rubber bands between the attachments. As an alternative to interconnection of the attachments with rubber bands looped over same, elastic thread, elastomeric monofilament string, or elastomeric molded members may be suitably secured to the attachments.

The illustrated arches in the embodiment of FIGS. 1 to 7 have the upper and lower first bicuspids extracted, thereby leaving the centrals, laterals, canines, second bicuspids, first and second molars. It can be appreciated that the present invention applies to any arches, whether or not there are extractions or whether or not they differ from that illustrated herein. FIGS. 1 to 6 show attachements in the form of brackets on the upper canines and bicuspids and the lower bicuspids and tubes on the upper and lower first molars. The attachments may take any form capable of receiving a looped end of a rubber band, a resilient string, or an elastomeric member, and they may be suitably mounted on the teeth by banding or bonding. The rubber band 16 is interconnected between the bracket on the upper canine and the lower bicuspid, while a rubber band 17 in triangular form is interconnected over the bracket on the upper bicuspid, and the tubes on the upper and lower first molars. Accordingly, the surfaces of the upper canines, bicuspids and first molars, and the lower bicuspids and first molars are necessarily exposed by the resilient appliance 15 being formed in the area of these teeth to accommodate the rubber bands 16 and 17. At the same time to provide the best possible working appliance 15, the portions of the appliance in the area of the anterior teeth are such as to cover at least a good portion of the labial surfaces thereof as well as part of the lingual surfaces of the anterior teeth of both arches to provide substantial socket structure for those teeth. FIG. 6 is a cross section taken through the appliance mesial to the upper left first molar and looking distally while the lower first molar would be sectioned as shown. This view illustrates the application of an occlusal vertical force on the buccal surface of the upper first molar to move its buccal cusp(s) into the occluder. If the lingual cusp(s) needed to be occluded, a lingual elastic would be placed to pull its lingual cusp(s) into its respective socket in the resilient appliance. Application of the elastics or rubber bands, as shown in FIGS. 1 and 2, would also encourage the maintenance of a class I interarch relationship when prior treatment has corrected a class II relationship.

To additionally understand the operation of the present invention, reference is made to FIG. 7 where the arrows indicate directions of vertical corrective forces that apply to the teeth for the case illustrated in FIGS. 1 to 6 when the appliance is first worn with the rubber bands to initiate finishing treatment. This is an exaggerated illustration showing the appliance 15 striking or engaging the total occlusal surfaces of the upper and lower anteriors, and the upper and lower second molars. The mesial cusps of the upper and lower first molars are engaged by the appliance. The upper and lower bicuspids are completely out of contact with the appliance. This is an illustration of treating a patient who had the first four bicuspids extracted. Vertical pull forces generated from the elastics would cause eruption or uprighting of those teeth not totally sealed until they fully seat in the bottoms of the respective sockets. Two elastics or rubber bands would be applied to the side looking at FIG. 7, as shown in FIGS. 1 and 2. It will be appreciated that the size of elastics applied would be selected to vary the amount of eruptive and depressive forces desired on individual teeth or combinations of teeth. This arrangement would help balance the occlusal forces on the teeth. With the arrangement of elastics as shown in FIG. 1 and applied to the situation shown in FIG. 7 and referring only to one side of the arches, the anterior teeth, the mesial cusps of the upper and lower first molars, and the upper and lower second molars would receive depressing forces equal to the total pull or traction forces of the elastics. Should the patient exercise into the appliance, the depressive forces would surpass total eruptive forces by the amount of muscular pressure applied. The eruptive forces would, of course, be applied to the bicuspids to erupt them vertically and to the distal cusps of the upper and lower first molars to change their mesial-distal inclinations until they would be in complete contact with the surface of the appliance. If the lower second molar also needed eruptive force, it could be accomplished in two different arrangements. In one arrangement three elastics could be employed, one between the upper first molar and the lower second molar, another between the upper bicuspid and the lower first molar, and a third between the upper canine and the lower bicuspid. Another system would utilize two triangularly formed elastics wherein one would interconnect the upper canine and bicuspid with the lower bicuspid and another would connect the upper first molar with the lower first and second molars. However, with respect to the second arrangement, the upper canine may be rotated by the distal pull of the horizontal section of the anterior elastics unless an archwire is left in the upper arch and engaged in the upper canine bracket.

While the present invention is capable of moving the teeth, it will be appreciated that the sockets of the resilient appliance 15, by virtue of being formed to mate with all of the occlusal surfaces of the teeth and at least part of the labial/buccal and lingual surfaces of some of the teeth, will also apply other slight movements to the teeth. For example, if the fixed appliances are banded, it would be necessary to close the spaces and the appliance 15 would assist in closing those spaces. However, if the fixed appliances were bonded to the teeth, those spaces would already be in closed position. By virtue of possible misalignment between the occlusal surfaces of the teeth and appliance, it may be necessary to slightly move at least some of the teeth labially, buccally or lingually, and such would be accomplished by virtue of the ideal alignment of the sockets in the archways of the resilient appliance.

As already explained, the elastomeric appliance 15 fitting interocclusally between the upper and lower arches functions like a custom-formed archwire for leveling of the teeth and moving them to the best possible occlusion, as the teeth will move to seat in the sockets so that the occlusal teeth surfaces fully seat in mating occlusal appliance surfaces. Thus, the forces that would be transmitted by the resilient appliance 15, together with the forces generated by the elastics attached to the opposed teeth, bring the teeth of both arches into the ideal occlusal positions desired at the end of treatment. This levels out the teeth in the arches as well as brings them into the ideal arch relationship.

If it would be desired to apply an elastic at the lingual surfaces of the teeth, as illustrated by the embodiment in FIG. 9, suitable attachments 27 and 28 are mounted on the lingual surfaces of the upper and lower teeth and interconnected by the rubber band 29. In addition to bringing the occlusal surfaces to the best possible position, movement of the teeth may also be accomplished to close spaces and to cause slight labial/lingual movement. It should also be appreciated that an archwire could be left on the upper arch or the lower arch or both arches if further control of root movement is desired, and the appliance would still function to give the best possible occlusion if the bracket-archwire relationship were such to permit the type of changes desired.

Use of the present invention by a patient is relatively simple since it is usually only necessary to insert the resilient appliance into the mouth in position on the arches and then attach the rubber bands to existing attachments fixed to the teeth. As already mentioned, the patient need not exercise into the resilient appliance as the forces necessary to obtain occlusion come from the rubber bands. Thus, passive use of the invention achieves occlusion, and soon after the teeth have moved to their proper occlusal positions, the attachments and elastics can be sequentially removed until the appliance is worn passively with no elastics for retention. Or, retention can be achieved with one of the well known types of rigid retainers, either fixed or removable.

In the event a patient was an open-bite case prior to treatment or even near the end of treatment, it might then be advisable to construct a resilient appliance of the type illustrated in FIG. 8 and designated by the numeral 15A where the labial surfaces of the anterior teeth are also exposed so that they may have attachments mounted thereon for interconnecting rubber bands between the upper and lower arches. The elastics not only pull the anterior teeth into occlusion but also provide labial-lingual control if necessary. It will be noted that the centrals, the laterals, the canines of the upper and lower arches have mounted on the labial surfaces attachments in the form of buttons 30 so that rubber bands 31 may be connected between attachments on the upper arch and attachments on the lower arch as illustrated to subject those teeth to tractive or pulling forces toward the appliance 15A. The posterior teeth would receive reciprocal forces through contact with the resilient appliance 15A. If the patient exercised in the resilient appliance, the total depressive forces on all teeth would exceed the total eruptive forces to aid in correction of relative vertical discrepancies between the anterior and posterior teeth.

The cross-sectional view of FIG. 9 illustrates the application of a rubber band at the lingual side of the appliance 15 as above described. Actually, the cross-sectional view in FIG. 9 on any one plane would not show both bracket or buttons unless the plane is along that of the elastic or rubber band which does not extend vertically. In this view, the vertical pull from the elastic 29 is used to both change the buccal/lingual inclination of the lower molar and bring the lingual cusps up into occlusion. The use of this form would require the patient to connect the elastic to the attachments prior to placement of the appliance 15.

The embodiment of FIG. 10 illustrates another manner of producing forces for leveling the teeth with a resilient appliance as previously described and which here is generally identified by the numeral 35. The general form of the resilient appliance 35 is like that shown in the first embodiment of FIGS. 1 to 7 for illustration purposes, and it differs, however, in that it includes a magnet molded within the interocclusal portion of the appliance which sits between the arches. This embodiment employs the principles of magnetism in that magnetic elements are employed in mounted relation on the teeth which will be attracted to the magnet bar 36 embedded in the resilient appliance 35. For example, the magnetic elements 37 are oriented so that they would be attracted to the magnet 36. These forces would be applied generally along the vertical to give directly eruptive and indirectly depressive forces to the teeth. Thus, the polarities of those magnet elements which would be attracted to the magnet bar 36 would be of unlike polarity with that of the adjacent side of the bar.

Another embodiment of the invention is illustrated in FIG. 11, wherein the resilient appliance to be positioned between the arches generally designated by the numeral 42 differs from the other appliances in that button attachments 43 and 44 are mounted on the upper and lower teeth and a force-generating member is in the form of a single elongated rubber band 45 mounted over the labial/buccal surface of the resilient appliance 42 through a plurality of positioning eyelets 46 and attached at opposite ends at the distal ends of the appliance onto hooks 47. The single rubber band could be replaced by a plurality of rubber bands each connected to a plurality of hooks along the labial/buccal surface of the appliance. It will now be appreciated that where an eruptive force is desired to be imparted to a tooth, a button or attachment is mounted on that tooth and one of the strands of the elongated rubber band 45 is then connected over the attachment, as shown by the three buttons 43 on the upper arch receiving a strand portion of the rubber band and two buttons 44 of the lower arch receiving a strand part of the rubber band. It will be appreciated that while the elastic 45 used may be in the form of an endless rubber band, it could also be in the form of a molded chain of elastomeric material or even an elastomeric monofilament string. It may be further recognized that this appliance can be used effectively for applying eruptive forces to a single arch, as it does not require that elastics interconnect between attachments on the upper and lower arches as in the previous embodiments utilizing elastics. Should a tooth in the opposite arch need occluding to the resilient appliance, an elastic would then be diverted around the button on that tooth.

A still further embodiment is illustrated in FIG. 12, wherein the resilient appliance is identified by the numeral 50 and otherwise takes generally the same shape as the appliance shown in FIGS. 1 to 7 for illustration purposes with the exception that where eruptive forces are needed, buttons 51 are mounted on the labial/buccal or lingual surfaces of the resilient appliance for attachment to buttons on either the teeth of the upper or lower arches, as illustrated by the buttons 52 on the upper arch and the button 53 on the lower arch. In this respect, elastics or rubber bands 54 and 55 interconnect buttons on the appliance to buttons on the teeth of the upper arch, while an elastic or rubber band 56 interconnects a button 51 on the resilient appliance to a button 53 on a tooth of the lower arch. Since the distance between the buttons is relatively short and the elastics therefore would be relatively small, the forces would be great or they would dissipate quickly. In any event, the embodiment would also accomplish the end result of producing eruptive forces on teeth in order to obtain the best possible occlusion by leveling the teeth and making them move into seated socket position of the resilient appliance.

The use of the present invention reduces, if not eliminates, the need for active patient exercising into a resilient appliance, while at the same time encourages the patient to cooperate and use the appliance so that the attachments can be removed as soon as possible since near the end of treatment, patients are extremely anxious to have the attachments removed. Accordingly, it can be seen that the present invention will significantly and efficiently result in the speedier precision finishing of orthodontic treatment.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance for achieving the best possible or ideal occlusion between the teeth of the arches comprising, resilient means to be placed between the arches and having occlusal tooth receiving archways which are arranged in the best possible or ideal occlusal positions, and means for applying eruptive forces to at least some of the teeth to coact with the resilient means and move the teeth into fully seated positions in said archways, said eruptive force applying means including anchor means mounted on the labial/- buccal or lingual surface of the teeth and the labial/buccal or lingual surface of the resilient means, and tensioned elastic means connected between the anchor means on the teeth and the anchor means on the resilient means.

2. An orthodontic appliance for achieving the best possible or ideal occlusion between the teeth of the arches comprising, resilient means to be placed between the arches and having occlusal tooth receiving archways which are arranged in the best possible or ideal occlusal positions, and means for applying eruptive forces to at least some of the teeth to coact with the resilient means and move the teeth into fully seated positions in said archways, said eruptive force applying means including magnet means mounted on at least one tooth, and magnet means embedded in the resilient means coacting with the magnet means on the tooth.

3. An orthodontic appliance to be used at or near the end of fixed appliance treatment for moving the teeth into the best possible occlusal positions, said orthodontic appliance comprising interocclusal means having an arch-shaped body of resilient material, upper and lower archways in said body having tooth receiving means for receiving the upper and lower arches of a person, said tooth receiving means being arranged in the best possible occlusal positions and having surfaces for mating with substantially all of the occlusal and at least a part of the labial/buccal and lingual surfaces of some of the teeth, and means for applying eruptive forces to at least one of the teeth of one of the arches to coact with the interocclusal means and move the teeth into fully seated positions in said tooth receiving means, said eruptive force applying means including one or more attachments mounted on teeth of one or both arches and a rubber band disposed horizontally over the labial/buccal surface of said body through guiding means and connected to the body for connection to one or more of said attachments.

4. An orthodontic appliance to be used at or near the end of fixed appliance treatment for moving the teeth into the best possible occlusal positions, said orthodontic appliance comprising interocclusal means having an arch-shaped body of resilient material, upper and lower archways in said body having tooth receiving means for receiving the upper and lower arches of a person, said tooth receiving means being arranged in the best possible occlusal position and having surfaces for mating with substantially all of the occlusal and at least a part of the labial/buccal and lingual surfaces of some of the teeth, and means for applying eruptive forces to at least one of the teeth of one of the arches to coact with the interocclusal means and move the teeth into fully seated positions in said tooth receiving means, said eruptive force applying means including one or more attachments mounted on teeth of one or both arches, one or more attachments mounted on said body, and tractive force producing elements connected at least between one of the attachments on one arch and one of the attachments on said body.

5. Orthodontic apparatus for achieving the best possible or ideal occlusion between the teeth of the upper and lower arches comprising, an appliance having a body of resilient material fitting interocclusally between the arches, and upper and lower archways and tooth sockets in the archways all of which are aligned in the best possible or ideal occlusal positions, said sockets having mating surfaces for receiving the occlusal surfaces of the teeth, and means for directly applying eruptive forces to at least some of the teeth to coact with the appliance and move the teeth into fully seated positions in said sockets, said eruptive force applying means including magnet members mounted on the labial/buccal or lingual surfaces of the teeth, and magnet means embedded in said appliance coacting with said magnet members.

6. Orthodontic apparatus for achieving the best possible or ideal occlusion between the teeth of the upper and lower arches comprising, an appliance having a body of resilient material fitting interocclusally between the arches, and upper and lower archways and tooth sockets in the archways all of which are aligned in the best possible or ideal occlusal positions, said sockets having mating surfaces for receiving the occlusal surfaces of the teeth, and means for directly applying eruptive forces to at least some of the teeth to coact with the appliance and move the teeth into fully seated positions in said sockets, said eruptive force applying means including attachments mounted on the labial/buccal or lingual surfaces of the teeth, attachments mounted on the labial/buccal surface of the appliance body, and tensioned resilient means connected between at least one attachment of a tooth and at least one attachment of said appliance body.

7. A method of orthodontically treating a patient to produce the best possible occlusion comprising the step of making an interocclusal resilient appliance from models of arches having the teeth arranged for the best possible occlusion to define occlusion areas into which the teeth can move, placing the appliance in the mouth of the patient, and interconnecting means to the teeth for applying eruptive forces to at least those teeth that are not seated in occlusion areas of the appliance to move them into seated position.

8. The method defined by claim 7, wherein the step of applying eruptive forces to at least some of the teeth includes the interconnection of tractive force generating elements between one or more teeth of one arch and one or more teeth of the other arch or the interocclusal resilient appliance.

9. A method of orthodontically treating a patient to produce the best possible occlusion comprising the step of constructing an orthodontic setup, making an interocclusal resilient appliance from the setup having occlusion areas into which the teeth can move to obtain the best possible occlusion, placing the appliance in the mouth of the patient, and interconnecting means to the teeth for applying eruptive forces to at least those teeth that are not seated in occlusion areas of the appliance to move them into seated position.

10. The method defined by claim 9, wherein the step of applying eruptive forces to at least some of the teeth includes the interconnection of tractive force generating elements between one or more teeth of one arch and one or more teeth of the other arch or the interocclusal resilient appliance.

* * * * *

UNITED STATES PATENT AND TRADEMARK OFFICE
CERTIFICATE OF CORRECTION

PATENT NO. : 4,330,273
DATED : May 18, 1982
INVENTOR(S) : Peter C. Kesling

It is certified that error appears in the above-identified patent and that said Letters Patent are hereby corrected as shown below:

```
Col. 2, line 23, change "moement" to --movement--;
Col. 5, line 57, after "when" insert --no--;
Col. 6, line 22, change "it" to --It--;
Col. 7, line 47, change "pullying" to --pulling--;
Col. 8, line 37, change "other" to --others--;
Col. 9, line 49, change "sealed" to --seated--;
Col. 12, line 15, change the second occurrence of "of"
                 to --on--; and
Col. 13, line 58, change "position" to --positions--.
```

Signed and Sealed this

Twenty-fourth Day of August 1982

[SEAL]

Attest:

GERALD J. MOSSINGHOFF

Attesting Officer

Commissioner of Patents and Trademarks